United States Patent [19]

Blaudin de THE et al.

[11] Patent Number: 5,149,781
[45] Date of Patent: Sep. 22, 1992

[54] STEROID/THYROID HORMONE RECEPTOR-RELATED GENE INAPPROPRIATELY EXPRESSED IN HUMAN HEPATOCELLULAR CARCINOMA

[75] Inventors: Hugues Blaudin de THE; Agnes Marchio; Pierre Tiollais; Anne Dejean, all of Paris, France

[73] Assignee: Institut Pasteur

[21] Appl. No.: 209,009

[22] Filed: Jun. 20, 1988

Related U.S. Application Data

[63] Continuation-in-part of Ser. No. 134,130, Dec. 17, 1987, which is a continuation-in-part of Ser. No. 133,687, Dec. 16, 1987, abandoned.

[51] Int. Cl.$^5$ .................. C07K 07/06; C07K 07/08; C07K 07/10; C07K 17/00; C07K 13/00
[52] U.S. Cl. .................. 530/326; 530/327; 530/328; 530/350; 530/405
[58] Field of Search ............... 530/350, 327, 328, 326, 530/405

[56] References Cited

FOREIGN PATENT DOCUMENTS 0244221 11/1987 European Pat. Off. .

OTHER PUBLICATIONS

Petkovich et al., "A Human Petinoic Acid Receptor which belongs to the Family of Nuclear Receptors" Nature v. 330, 444–450, Dec. 3, 1987.
Evans et al. Science 240 889–895 May 13, 1988.
de Thé et al. Nature 330 667–670 Dec. 17, 1987.
Benbrooh et al. Nature 333 669–672 Jun. 16, 1988.
Brand et al. Nature 332 850–853 Apr. 28, 1988.
Dejean et al. Nature 372 70–72 Jul. 3, 1986.

*Primary Examiner*—Margaret Moskowitz
*Assistant Examiner*—Nina Ossanna

[57] ABSTRACT

A previously isolated hepatitis B virus (HBV) integration in a 147 bp cellular DNA fragment linked to hepatocellular carcinoma (HCC) was used as a probe to clone the corresponding complementary DNA from a human liver cDNA library. Nucleotide sequence analysis revealed that the overall structure of the cellular gene, which has been named hap, is similar to that of the DNA-binding hormone receptors. Six out of seven hepatoma and hepatoma-derived cell-lines express a 2.5 kb hap mRNA species which is undetectable in normal adult and fetal livers, but present in all non-hepatic tissues analyzed. Low stringency hybridization experiments revealed the existence of hap related genes in the human genome. The cloned DNA sequence is useful in the preparation of pure hap protein and as a probe in the detection and isolation of complementary DNA and RNA sequences.

12 Claims, 5 Drawing Sheets

STEROID/THYROID HORMONE RECEPTOR-RELATED GENE INAPPROPRIATELY EXPRESSED IN HUMAN HEPATOCELLULAR CARCINOMA

CROSS-REFERENCE TO RELATED APPLICATIONS

This application is a continuation-in-part of application Ser. No. 134,130, filed Dec. 17, 1987, which is a continuation-in-part of application Ser. No. 133,687, filed Dec. 16, 1987, now abandoned. The entire disclosure of each of these copending applications is relied upon and incorporated herein by reference

BACKGROUND OF THE INVENTION

Primary hepatocellular carcinoma (HCC) represents the most common cancer, especially in young men, in many parts of the world (as in China and in much of Asia and Africa) (reviewed in Tiollais et al., 1985). Its etiology was investigated mostly by epidemiological studies, which revealed that, beyond some minor potential agents such as aflatoxin and sex steriod hormones, hepatitis B virus (HBV) chronic infection could account for a large fraction of liver cancers (Beasley and Hwang, 1984).

HBV DNA has been found to be integrated in the genome of most cases of HCCs studied (Edman et al., 1980; Brechot et al., 1980; Chakraborty et al., 1980; Chen et al., 1982). Nonetheless the role of those sequences in liver oncogenesis remains unclear.

A single HBV integration in a HCC sample in a short liver cell sequence has been reported recently. The sequence was found to be homologous to steroid receptor genes and to the cellular proto-oncogene c-erbA (Dejean et al., 1986).

Ligand-dependent transcriptional activators, such as steroid or thyroid hormone receptors, have recently been cloned allowing rapid progress in the understanding of their mechanism of action Nevertheless, there exists a need in the art for the identification of transcripts that may encode for activational elements, such as nuclear surface receptors, that may play a role in hepatocellular carcinoma. Such findings would aid in identifying corresponding transcripts in susceptible individuals. In addition, identification of transcripts could aid in elucidating the mechanisms by which HCC occurs.

SUMMARY OF THE INVENTION

This invention aids in fulfilling these needs in the art. More particularly, this invention provides a cloned DNA sequence encoding for a polypeptide of a newly identified cellular gene, which has been named hap. The DNA sequence has the formula shown in FIG. 2. More particularly, the sequence comprises:

```
ATGTTTGACTGTATGGATGTTCTGTCAGTGAGTCCTGGGCAAATCCTGATTCTACACTGC
GTCTTCCTGCATGCTCCAGGAGAAAGCTCTCAAAGCATGCTTCAGTGGATTGACCCAAAC
GCAGCATCGGCACACTGCTCAATCAATTGAAACACAGAGCACCAGCTCTGAGGAACTCGT
CCCCCCATCTCCACTTCCTCCCCCTCGAGTGATCAAACCCTGCTTCGTCTGCCAGGACAA
AGGGTACCACTATGGGGTCAGCGCCTGTGAGGGATGAAGGGCTTTTTCCGCAGAAGTATT
AATATGATTTACACTTGTCACCGAGATAAGAACTGTGTTATTAATAAAGTCACCAGGAAT
CAATACTGTCGACTCCAGAAGTGCTTTGAAGTGGGAATGTCCAAAGAATCTGTCAGGAAT
AACAAGAAAAAGAAGGAGACTTCGAAGCAAGAATGCACAGAGAGCTATGAAATGACAGCT
GACGATCTCACAGAGAAGATCCGAAAAGCTCACCAGGAAACTTTCCCTTCACTCTCGCAG
AAATACACCACGAATTCCAGTGCTGACCATCGAGTCCGACTGGACCTGGGCCTCTGGGAC
AGTGAACTGGCCACCAAGTGCATTATTAAGATCGTGGAGTTTGCTAAACGTCTGCCTGGT
GGCTTGACCATCGCAGACCAAATTACCCTGCTGAAGGCCGCCTGCCTGGACATCCTGATT
ATTTGCACCAGGTATACCCCAGAACAAGACACCATGACTTTCTCAGACGGCCTTACCCTA
ACTCAGATGCACAATGCTGGATTTGGTCCTCTGACTGACCTTGTGTTCACCTTTGCCAAC
CTGCCTTTGGAAATGGATGACACAGAAACAGGCCTTCTCAGTGCCATCTGCTTAATCTGT
CGCCAGGACCTTGAGGAACCGACAAAAGTAGATAAGCTACAAGAACCATTGCTGGAAGCA
ATTTATATCAGAAAAAGACGACCCAGCAAGCCTCACATGTTTCCAAAGATCTTAATGAAA
GATCTCCGTAGCATCAGTGCTAAAGGTGCAGAGCGTGTAATTACCTTGAAAATGGAAATT
TCAATGCCACCTCTCATTCAAGAAATGATGGAGAATTCTGAAGGACATGAACCCTTGACC
TCAAGTGGGAACACAGCAGAGCACAGTCCTAGCATCTCACCCAGCTCAGTGGAAAACAGT
AGTCAGTCACCACTCGTGCAATAA.
```

The invention also covers variants and fragments of the DNA sequence. The DNA sequence is in a purified form.

This invention also provides a probe consisting of a radionuclide bonded to the DNA sequence of the invention.

In addition, this invention provides a hybrid duplex molecule consisting essentially of the DNA sequence of the invention hydrogen bonded to a nucleotide sequence of complementary base sequence, such as DNA or RNA.

Further, this invention provides a polypeptide comprising an amino acid sequence of hap protein, wherein the polypepetide contains the amino acid sequence shown in FIG. 2. More particularly, the amino acid sequence comprises:

```
MetPheAspCysMetAspValLeuSerValSerProGlyGlnIleLeuAspPheTyrThr
SerProSerSerCysMetLeuGlnGluLysAlaLeuLysAlaCysPheSerGlyLeuThr
ThrGluTrpGlnHisArgHisThrAlaGlnSerIleGluThrGlnSerThrSerSerGlu
LeuValProSerProProSerProLeuProProProArgValTyrLysProCysPheVal
lnAspLysSerSerGlyTyrHisTyrGlyValSerAlaCysGluGlyCysLysGlyPheP
ArgArgSerIleGlnLysAsnMetIleTyrThrCysHisArgAspLysAsnCysValIle
LysValThrArgAsnArgCysGlnTyrCysArgLeuGlnLysCysPheGluValGlyMet
LysGluSerValArgAsnAspArgAsnLysLysLysLysGluThrSerLysGlnGluCys
GlySerTyrGluMetThrAlaGluLeuAspAspLeuThrGluLysIleArgLysAlaHis
GluThrPheProSerLeuCysGlnLeuGlyLysTyrThrThrAsnSerSerAlaAspHis
ValArgLeuAspLeuGlyLeuTrpAspLysPheSerGluLeuAlaThrLysCysIleIle
IleValGluPheAlaLysArgLeuProGlyPheThrGlyLeuThrIleAlaAspGlnIle
LeuLeuLysAlaAlaCysLeuAspIleLeuIleLeuArgIleCysThrArgTyrThrPro
```

-continued

GlnAspThrMetThrPheSerAspGlyLeuThrLeuAsnArgThrGlnMetHisAsnAla
PheGlyProLeuThrAspLeuValPheThrPheAlaAsnGlnLeuLeuProLeuGluMet
AspThrGluThrGlyLeuLeuSerAlaIleCysLeuIleCysGlyAspArgGlnAspLeu
GluProThrLysValAspLysLeuGlnGluProLeuLeuGluAlaLeuLysIleTyrIle
LysArgArgProSerLysProHisMetPheProLysIleLeuMetLysIleThrAspLeu
SerIleSerAlaLysGlyAlaGluArgValIleThrLeuLysMetGluIleProGlySer
ProProLeuIleGlnGluMetMetGluAsnSerGluGlyHisGluProLeuThrProSer
SerGlyAsnThrAlaGluHisSerProSerIleSerProSerSerValGluAsnSerGly
SerGlnSerProLeuValGln.

The invention also covers serotypic variants of the polypeptide and fragments of the polypeptide. The polypeptide is free from human serum proteins, virus, viral proteins, human tissue, and human tissue components. Preferably, the polypeptide is free from human, blood-derived protein.

Also, this invention provides a process for selecting a nucleotide sequence coding for hap protein or a portion thereof from a group of nucleotide sequences comprising the step of determining which of the nucleotide sequences hybridizes to a DNA sequence of the invention. The nucleotide sequence can be a DNA sequence or an RNA sequence. The process can include the step detecting a label on the nucleotide sequence.

Still further, this invention provides a recombinant vector comprising lambda-NM1149 having an EcoRI restriction endonucleas site into which has been inserted the DNA sequence of the invention. The invention also provides plasmid pCOD20, which comprises the DNA sequence of the invention.

Finally, this invention provides an *E. coli* bacterial culture in a purified form, wherein the culture comprises *E. coli* cells containing DNA, wherein a portion of the DNA comprises the DNA sequence of the invention. Preferably, the *E. coli* is strain TG-1.

BRIEF DESCRIPTION OF THE DRAWINGS

This invention will be described in greater detail with reference to the drawings in which

FIG. 2 is the nucleotide sequence of human liver hap cDNA and a predicted amino acid sequence of human liver hap cDNA;

FIG. 6 shows the alignment of hap translated amino acid sequence with several known sequences for thyroid and steroid hormone receptors;

DETAILED DESCRIPTION OF PREFERRED EMBODIMENTS

As previously noted, ligand-dependent transcriptional activators, such as steroid or thyroid hormone receptors, have recently been cloned. The primary structure and expression of a new gene, hap, closely related to steroid or thyroid hormone receptor genes have now been discovered. The hap product exhibits two regions highly homologous to the conserved DNA- and hormone-binding domains of previously cloned receptors.

More particularly, the cloning of a cDNA corresponding to a novel steroid/thyroid hormone receptor-related gene has been achieved. The cDNA was recovered from a human liver cDNA library using a labelled cellular DNA fragment previously isolated from liver tumor. The fragment contained a 147 bp putative exon in which HBV inserted. The sequence of this cellular gene, which is referred to herein as hap for hepatoma, reveals various structure features characteristic of c-erbA/steroid receptors (Dejean e al , 1986). The receptor-related protein is likely to be a novel member of the superfamily of transcriptional regulatory proteins that includes the thyroid and steroid hormone receptors It has been discovered that the hap gene is transcribed at low level in most human tissues, but the gene is overexpressed in prostate and kidney. Moreover, six out of seven hepatoma and hepatoma-derived cell lines express a small hap transcript, which is undetectable in normal adult and fetal livers, but is present in all non-hepatic tissues tested. Altered expression of hap may be involved in liver oncogenesis.

These findings, as well as other discoveries relating to this invention, will now be described in detail.

Cloning and Sequencing of a Hap cDNA

A human liver cDNA library was screened using a nick-translated 350 bp EcoRI genomic fragment (MNT probe) previously cloned from a hepatoma sample. The fragment contained the putative 147 bp cellular exon in which HBV integration took place (Dejean et al., 1986).

Four positive 3' co-terminal clones were isolated from the $2 \times 10^6$ plaques screened and the restriction maps were deduced for each of the cDNA clone EcoRI inserts. The longest one was identified lambda-13. The restriction map of lambda-13 is shown in FIG. 1.

Figure 1:
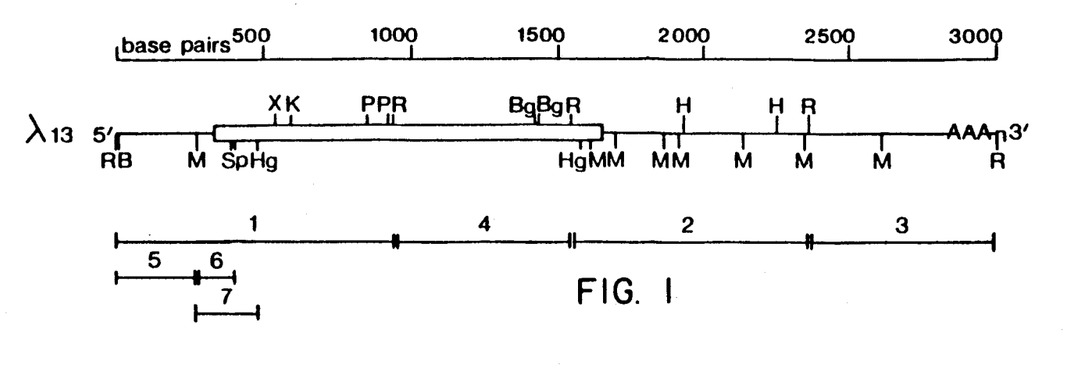
FIG. 1 is a restriction map of human liver hap cDNA.

Referring to FIG. 1, the insert of clone lambda-13 is nearly a full-length cDNA for the hap gene. Noncoding sequences (lines and coding sequences (boxed portion) are indicated. Restriction sites are:

R EcoRI
Bg BglII
M MaeI
X XhoI
K KpnI
P PvuII
B BamHI
H HindIII.

The lambda-13 clone was subjected to nucleotide sequence analysis. The nucleotide sequence is shown in FIG. 2. The nucleotide sequence of the hap cDNA is presented in the 5' to 3' orientation. The numbers on the right refer to the position of the nucleotides. Numbers above the deduced translated sequence indicate amino acid residues. The four short open reading frame in the 5' untranslated region are underlined. Adenosine residues (20) are found at the 3' end of lambda-13. The putative polyadenylation signal site (AATAAA) is boxed. The region homologous to the DNA-binding domain of known thyroid/steroid hormone receptors is indicated by horizontal arrows. The exon, previously cloned from a HCC sample genomic DNA library and in which HBV integration took place, is bracketed.

This invention of course includes variants of the nucleotide sequence shown in FIG. 2 encoding hap protein or a serotypic variant of hap protein exhibiting the same immunological reactivity as hap protein.

The DNA sequence of the invention is in a purified form. Generally, the DNA sequence is free of human serum proteins, viral proteins, and nucleotide sequences encoding these proteins The DNA sequence of the invention can also be free of human tissue.

The DNA sequence of the invention can be used as probe for the detection of a nucleotide sequence in a biological material such as tissue or body fluids. The polynucleotide probe can be labeled with an atom or inorganic radical, most commonly using a radionuclide, but also perhaps with a heavy metal.

In some situations it is feasible to employ an antibody which will bind specifically to the probe hybridized to a single stranded DNA or RNA. In this instance, the antibody can be labeled to allow for detection. The same types of labels which ar used for the probe can also be bound to the antibody in accordance with known techniques.

Conveniently, a radioactive label can be employed. Radioactive labels include $^{32}P$, $^{3}H$, $^{14}C$, or the like. Any radioactive label can be employed, which provides for an adequate signal and has sufficient half-life. Other labels include ligands, that can serve as a specific binding member to a labeled antibody, fluorescers, chemiluminescers, enzymes, antibodies which can serve as a specific binding pair member for a labeled ligand, an the like. The choice of the label will be governed by the effect of the label on the rate of hybridization and binding of the probe to the DNA or RNA. It will be necessary that the label provide sufficient sensitivity to detect the amount of DNA or RNA available for hybridization.

Liqands and anti-ligands can be varied widely. Where a ligand has a natural receptor, namely ligands such as biotin, thyroxine, and cortisol, these ligands can be used in conjunction with labeled naturally occurring receptors. Alternatively, any compound can be used, either haptenic or antigenic, in combinations with an antibody.

Enzymes of interest as labels are hydrolases, particularly esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin and luminol.

Amino Acid Sequence of Protein Encoded by hap Gene

Based upon the sequence of the hap cDNA, the amino acid sequence of the protein encoded by hap gene was determined. With reference to FIG. 2, the deduced amino acid sequence encoded by the gene reveals a long open reading frame of 448 amino acids corresponding to a predicted polypeptide of relative molecular mass 51,000.

A putative initiator methionine codon and an inframe terminator codon are positioned respectively at nucleotides 322 and 1666 in the sequence (FIG. 2). However, two other methionine codons are found 4 and 26 triplets downstream from the first ATG making the determination of the initiation site equivocal.

The coding sequence is preceded by a 5' region of at least 321 nucleotides which contains four short open reading frames delineated by initiator and stop codons (FIG. 2). Translation usually starts, in eukaryotes, at the 5' most ATG triplet, but the finding of open reading frames in the 5' 'untranslated' region is not unprecedented (Kozak, 1986). It is not known yet whether those sequences are used for translation and exert any function in the cell.

In the 3' untranslated region, 1326 nucleotides long, no long open reading frame is present. A putative polyadenylation signal (AATAAA) is found 19 bp upstream from the polyadenylation site.

It will be understood that the present invention is intended to encompass the protein encoded by the hap gene, i.e. hap protein, and fragments thereof in highly purified form. The hap protein can be expressed in a suitable host containing the DNA sequence of the invention. This invention also includes polypeptides in which all or a portion of the binding site of hap protein is linked to a larger carrier molecule, such as a polypeptide or a protein, and in which the resulting product exhibit specific binding in vivo and in vitro. In this case, the polypeptide can be smaller or larger than the proteinaceous binding site of the protein of the invention.

It will be understood that the polypeptide of the invention encompasses molecules having equivalent peptide sequences. By this it is meant that peptide sequences need not be identical. Variations can be attributable to local mutations involving one or more amino acids not substantially affecting the binding capacity of the polypeptide. Variations can also be attributable to structural modifications that do not substantially affect binding capacity. Thus, for example, this invention is intended to cover serotypic variants of hap protein.

Three particular regions of hap gene are of interest. Two of them are located in the D region (amino acids comprised between 147 and 196), which have been shown by the inventors to be highly immunogenic. Amino acids 46–196 have the sequence:

GlnHisArgHisThrAlaGlnSerIleGluThrGlnSerThrSerSerGluGlu
LeuValProSerProProSerProLeuProProProArgValTyrLysProCysPheVal
GlnAspLysSerSerGlyTyrHisTyrGlyValSerAlaCysGluGlyCysLysGlyPhe
ArgArgSerIleGlnLysAsnMetIleTyrThrCysHisArgAspLysAsnCysValIle
LysValThrArgAsnArgCysGlnTyrCysArgLeuGlnLysCysPheGluValGlyMet
LysGluSerValArgAsnAspArgAsnLysLysLysLysGluThrSerLysGlnGluCys
GluSerTyrGluMetThrAlaGluLeuAspAspLeuThrGluLysIleArgLysAlaHis
GluThrPheProSerLeuCys.

One peptide of interest in the D region is comprised of acids 151–167 and has the sequence:

ValArgAsnAspArgAsnLysLysLysLysGluThrSerLysGlnGluCys.

A second peptide in the D region is located between amino acids 175 and 185. This peptide has the amino acid sequence:

AlaGluLeuAspAspLeuThrGluLysIleArg.

Another peptide of interest is located at the end of C-terminal region between (E region) between amino acids 440 and 448. This peptide has the amino acid sequence:

GlyValSerGlnSerProLeuValGln.

Other peptides having formulas derived from the nucleotide sequence of hap gene can be used as reagents, particularly to obtain antibodies for diagnostic purposes, as defined hereinabove The most favorable region is found in the hinge region (amino acids 147 to 193). This region includes amino acids 150 to 170, corresponding to the following criteria:

The region includes very hydrophilic sequences, namely the sequences 154-160 (No. 1/Hopp); 155-161 (No. 1/Doolittle); 155-159 (No. 1/acrophilic).

The region includes a peptide, namely, amino acids 156-162, No. 5 in mobility.

The polypeptide of this region has a low probability of adopting a structure in the form of a folded sheet or a helix, but, in contrast, a good probability of an omega loop and one beta-turn, very marked in the Asp-Arg-Asn-Lys tetrapeptide.

The region does not have a potential site of N-glycosylation nearby; several suggestions in this zone can be made:

Val—Arg—Asn—Asp—Arg—Asn—Lys—Lys—Lys—Glu—Thr—Ser—Lys—Gln—Glu—Cys (peptide 1);

Peptide 1 corresponds to amino acids 151-167 and permits finding Cys 167, which is present in the sequence and enables attachment to a carrier (it will be noted that this peptide corresponds to consensus sequence of phosphorylation by kinase A).

Peptide 1 can be shortened by N-turn while preserving the beta-turn and by C-turn while replacing Ser by Cys to maintain the possibility of coupling at this level:

Asn-Asp-Arg-Asn-Lys-Lys-Lys-Glu-Thr-Cys
(peptide 2).

Peptide 2 is also favorable, but is clearly less favorable than Peptide 1 from the viewpoint of hydrophilicity as of its higher potential for spatial organization (probably as amphiphilic helix).

Finally, it will be noted that the C-terminal end constitutes a preferred region as a function of its mobility, but it nevertheless remains very hydrophobic. For example, the following peptide is contemplated:

Cys-Gly-Val-Ser-Gln-Ser-Pro-Leu-Val-Gln (peptide 3).

Peptide 3 can be fixed in a specific manner by an N-terminal Cys in such a way as to reproduce its aspect on the protein.

The nucleotide sequences of hap gene encoding those peptides are as follows:
For peptide 1:

GTCAGGAATGACAG-
GAACAAGAAAAAGAAGGAGACTT-
CGAAGCAAGAATGC.

For peptide 2:

GGGGTCACTCAGTCACCACTCGTGCAA.

For peptide 3:

AATGACAGGAACAAGAAAAAGAAG-
GAGACT.

For peptide of amino acids 175-185:

GCTGAGTTGGACCATCT-
CACAGAGAAGATTCCGA.

The polypeptides of the invention can be injected in mice, and monoclonal and polyclonal antibodies can be obtained. Classical methods can be used for the preparation of hybridomas. The antibodies can be used to quantify the amount of human receptors produced by patients in order to correlate the pathological states of illness and quantity of receptors or the absence of such receptors.

Epitope-bearing polypeptides, particularly those whose N-terminal and C-terminal amino acids are free, are accessible by chemical synthesis using techniques well known in the chemistry of proteins. For example, the synthesis of peptides in homogeneous solution and in solid phase is well known.

In this respect, recourse may be had to the solid phase synthesis of peptides using the method of Merrifield, J. Am. Chem. Assoc. 85, 2149-2154 (1964) or the method of synthesis in homogeneous solution described by Houbenweyl in the work entitled "Methoden der Organischen Chemie" (Methods of Organic Chemistry) edited by E. WUNSCH, vol. 15-I and II, THIEME, Stuttgart (1974).

This method of synthesis consists of successively condensing either the successive amino acid in pairs in the appropriate order, or successive peptide fragments previously available or formed and containing already several aminoacyl residues in the appropriate order, respectively. Except for the carboxyl and amino groups which will be engaged in the formation of the peptide bonds, care must be taken to protect beforehand all other reactive groups borne by these aminoacyl groups and fragments. However, prior to the formation of the peptide bonds, the carboxyl groups are advantageously activated according to methods well known in the synthesis of peptides. Alternatively, recourse may be had to coupling reactions bringing into play conventional coupling reagents, for instance of the carbodiimide type such as 1-ethyl-3-(3-dimethyl-aminopropyl)-carbodiimide. When the amino acid group carries an additional amino group (e.g. lysine) or another acid function (e.g. glutamic acid), these groups may be protected by carbobenzoxy or t-butyloxycarbonyl groups, as regards the amino groups, or by t-butylester groups, as regards the carboxylic groups. Similar procedures are available for the protection of other reactive groups. For example, SH group (e.g in cysteine) can be protected by an acetamidomethyl or paramethoxybenzyl group.

In the case of progressive synthesis, amino acid by amino acid, the synthesis preferably starts by the condensation of the C-terminal amino acid with the amino acid which corresponds to the neighboring aminoacyl group in the desired sequence and so on, step by step, up to the N-terminal amino acid. Another preferred technique that can be relied upon is that described by R. D. Merrifield in "Solid Phase Peptide Synthesis" (J. Am. Chem. Soc., 45, 2149-2154). In accordance with the Merrifield process the first C-terminal amino acid of the chain is fixed to a suitable porous polymeric resin by means of its carboxylic group, the amino group of said amino acid then being protected, for example by a t-butyloxycarbonyl group.

When the first C-terminal amino acid is thus fixed to the resin, the protective group of the amino group is removed by washing the resin with an acid, i.e. trifluoroacetic acid when the protective group of the amino group is a t-butyloxycarbonyl group.

Then the carboxylic group of the second amino acid, which is to provide the second aminoacyl group of the desired peptide sequence, is coupled to the deprotected amino group of the C-terminal amino acid fixed to the resin. Preferably, the carboxyl group of this second amino acid has been activated, for example by dicyclohexylcarbodiimide, while its amino group has been protected, for example by a t-butyloxycarbonyl group. The first part of the desired peptide chain, which comprises the first two amino acids, is thus obtained. As previously, the amino group is then deprotected, and one can further proceed with the fixing of the next aminoacyl group and so forth until the whole peptide sought isobtained.

The protective groups of the different side groups, if any, of the peptide chain so formed can then be removed. The peptide sought can then be detached from the resin, for example, by means of hydrofluoric acid, and finally recovered in pure form from the acid solution according to conventional procedures.

Depending on the use to be made of the proteins of the invention, it may be desirable to label the proteins. Examples of suitable labels are radioactive labels, enzymatic labels, flourescent labels, chemiluminescent labels, or chromophores. The methods for labeling proteins of the invention do not differ in essence from those widely used for labeling immunoglobulin.

Tissue Specific mRNA Distribution

In order to study expression of the hap gene, Northern blot analysis was performed using MNT as a probe and poly(A)+ RNA extracted from various human tissues and cell lines. The result are shown in FIG. 3.

More particularly, Northern blot analyses were performed with poly(A)+ RNAs (15 µg per lane) extracted from different human organs and cell lines. A control hybridization with a mouse beta-actin cDNA probe is shown below the hybridizations in FIG. 3.

Hap mRNA in different tissues is shown in FIG. 4A as follows
Lane a ovary
Lane b uterus
Lane c HBL 100 mammary cells
Lane d adult spleen
Lane e 18 weeks fetal spleen
Lane f K562
Lane g HL60 hematopoeitic cell lines
Lane h prostatic adenoma
Lane l kidney
Lane j adult liver
Lane k 18 weeks fetal liver.
Lanes a-k correspond to a one day exposure.

Figure 3:
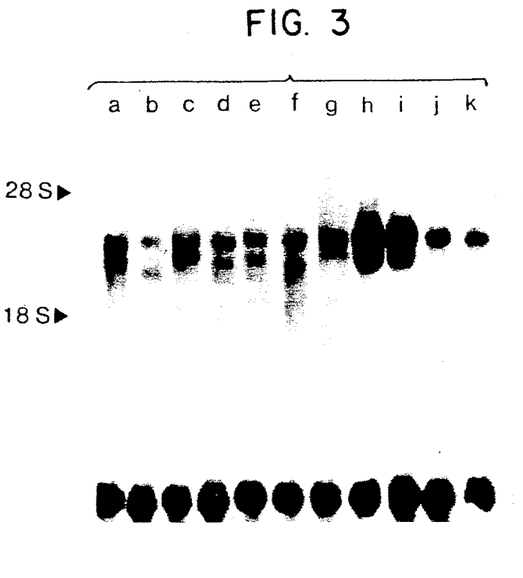
FIG. 3 depicts the distribution of hap mRNA in different tissues as determined by Northern blot analysis.

FIG. 3 shows that two RNA species of 3 kb and +2.5 kb (the size of this smaller mRNA is slightly variable from one organ to another) were expressed at low abundance in ovary (lane a), uterus (lane b), HBL 100 mammary cells (lane c), adult and fetal spleen (lane d and e, respectively), and K562 and HL60 hematopoeitic cell lines (lanes f and g, respectively). Surprisingly, an approximately tenfold higher level of expression was detected in prostatic adenoma (lane h) and kidney (lane i). By contrast, a single mRNA of 3000 nucleotides, expressed at low levels, was present in poly(A)+RNA from adult and fetal liver tissues (lanes j and k). Therefore, the cloned hap cDNA is likely to be a full-length copy of this transcript.

The finding of two mRNA species overexpressed in prostate and kidney, as well as the presence of a single mRNA expressed a low level in adult and fetal livers show that hap expression is differentially regulated in those organs. This tissue specific expression provides some indication that prostate and kidney, as well as liver, could be key tissues and that hap functions in those cell types may differ.

Figure 4:
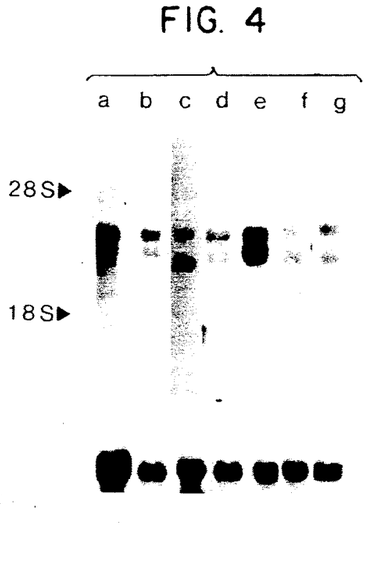
FIG. 4 depicts the distribution of hap mRNA in HCC and HCC derived cell lines as determined by Northern blot analysis.

FIG. 4 shows hap mRNA in HCC and HCC derived cell-lines as follows:
Lane a, normal liver (four days autoradiography);
Lanes b, c, d: three HCC samples (Lane b, patient Ca; Lane c, patient Mo; Lane d, patient TCl);
Lanes e, f, g: three HCC-derived cell lines (Lane e, PLC/PRF/5; Lane f, HEPG2; Lane g, HEP 3B).
The lanes b-g correspond to a one day exposure. Once again, a control hybridization with a normal beta-actin cDNA probe is shown below the hybridizations.

With reference to FIG. 4, the smaller 2.5 kb mRNA was undetectable, even after long exposure, in three adult and two fetal human livers analyzed (FIG. 4, Lane a). This differential expression in normal livers may suggest a distinct role of hap in this particular tissue.

Northern blot analysis of human HCCs and hepatoma cell line showed almost constant alterations in hap transcription. There are two possible alternatives to explain this result. The smaller mRNA species can be simply expressed as a consequence of the cellular dedifferentiation. The tumorous liver cell, having lost its differentiated characteristics, would behave as any other cell type and thus express the same 2.5 kb mRNA as found i non-hepatic cells. However, the inability to detect such a smaller transcript in fetal livers does not seem to favor this hypothesis. On the contrary, the presence of the smaller transcript may have preceded the tumorigenesis events and would rather reflect a preneoplastic state. The presence of an inappropriately expressed hap protein, normally absent from normal hepatocytes, may have directly participated to the hepatocellular transformation. In this respect, the previous study reporting a HBV integration in the hap gene of a human HCC (Dejean et al., 1986) strongly supports the idea that hap could be causatively involved in liver oncogenesis. Indeed, in this tumor, a chimeric gene between the viral pre-S1 gene and hap may have resulted in the overexpression of a truncated hap protein. At present, it is the one found in non-hepatic tissues.

Expression of hap in Hepatocellular Carcinoma

Hap was first identified in a human primary liver cancer. Encouraged by this finding, poly(A)+RNA from seven hepatoma and hepatoma-derived cell lines were analyzed by Northern-blotting. Five of them contained integrated HBV DNA sequences. In addition to the 3 kb long mRNA found in normal adult and fetal liver, an additional +2.5 kb RNA species was observed, in equal or even greater amount, in three out of four HCC (FIG. 4, Lanes b, c, d) and in the PLC/PRF/5, HEPG2 and HEP3B hepatoma cell-lines (Lanes e, f, g). The size of the smaller transcript was variable from sample to sample. In addition, the two transcripts were strikingly over-expressed, at least ten fold, in the PLC/PRF/5 cells.

To test the possibility that the inappropriate expression of hap in those six tumors and tumorous cell-lines might be the consequence of a genomic DNA alteration, Southern-blotting of cellular DNA was performed using, as two probes, the MNT fragment together with a 1 kb EcoRI fragment corresponding to the 5' extremity of the cDNA insert (FIG. 2). No rearrangement and/or amplification was detected with any of these two probes which detect a different single exon (data not shown), suggesting that the hap gene was not altered at the genomic level. It is yet unknown whether the +2.5 kb mRNA, present in the liver tumorous samples and cell lines, corresponds to the same smaller transcript as that found in non-hepatic tissues. However, its presence in the liver seems to be clearly associated to the hepatocellular transformed state.

Hormone-binding Assay

Amino-acid homologies between the hap protein and the c-erbA/steroid receptors support the hypothesis that hap may be receptor for a thyroid/steroid hormone-related ligand. The ability to express functional receptors in vitro from cloned c-erbA/steroid receptor genes led to the use of an in vitro translation assay to identify a putative hap ligand.

Figure 5:
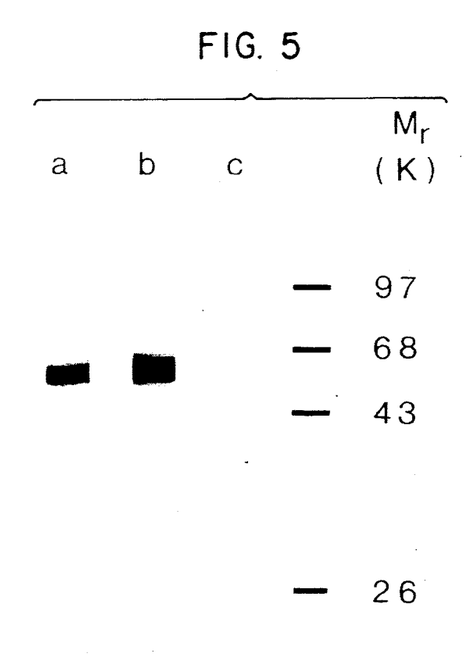
FIG. 5 is a fluorograph of hap polypeptide synthesized in vitro and isolated on SDS-polyacrylamide gel.

The coding region of hap was cloned into pTZ18 plasmid vector to allow in vitro transcription with the T7 RNA polymerase and subsequent translation in reticulocyte lysates. The results are shown in FIG. 5. More particularly, $^{35}$S-methionine-labelled products synthesized using T7 polymerase-catalysed RNA transcripts were separated on a 12% SDS-polyacrylamide gel, which wa fluorographed (DMSO-PPO). The lanes in FIG. 5 are as follows:

Lane a, pCOD 20 (sense RNA, 70 ng)
Lane b, pCOD 20 (140 ng)
Lane c, pCOD 14 (antisense RNA, 140 ng).

FIG. 5 shows that the hap RNA directed the efficient synthesis of a major protein, with a 51 K relative molecular mass, consistent with the size predicted by the amino acid sequence (lanes a and b), whereas the antisense RNA-programmed lysate gave negligible incorporation (lane c).

Because c-erbA and hap colocalize on chromosome 3 and are more closely related according to their amino acid sequence, ($^{125}$I)-T3 (triiodothyronine), -reverse T3 (3,3',5'-triiodothyronine) and -T4 (thyroxine), were first tested for their binding with the in vitro translated hap polypeptide. No specific fixation with any of those three thyroid hormones could be detected. As a positive control, binding of a T3 was detected with nuclear extracts from HeLa cells. The results were negative as well when the experiment was repeated with (3H)-retinol, -retinoic acid, and -testosterone, which represent three putative ligands for hap whose receptors have not yet been cloned. Although it cannot excluded that hap may encode a hormone independent transcriptional activator, it is more likely that hap product, i.e. the hap protein, is a receptor for a presently unidentified hormone.

Similarity of HAP Protein to Thyroid/Steroid Hormone Receptors

The c-erbA gene product, recently identified as a receptor for thyroid hormone (Weinberger, et al., 1986; Sap et al., 1986) as well as the steroid receptors, belong to a superfamily of regulatory proteins, which consequently to their binding with specific ligand, appear capable of activating the transcription of target genes (reviewed by Yamamoto, 1985). This activation seem to be the result of a specific binding of the hormone-receptor complex to high-affinity sites on chromatin.

Comparative sequence analysis has been made between the following different cloned steroid receptors:

glucocorticoid receptor (GR) (Hollenberg et al., 1985; Miesfeld et al., 1986);

oestrogen receptor (ER) (Green et al., 1986; Greene et al., 1986);

progesterone receptor (PR) (Conneely et al., 1986; Loosfelt et al., 1986); and thyroid hormone receptor (c-erbA product) (Weinberger et al., 1986; Sap et al., 1986).

Mutation analysis has also been carried out. (Kumar et al., 1986; Hollenberg et al., 1987; Miesfeld et al., 1987). The results revealed the presence of two conserved regions representing the putative DNA-binding and hormone-binding domains of those molecules. It has now been discovered that hap protein is homologous to the thyroid/steroid hormone receptors.

More particularly, homology previously reported between the putative 147 bp cellular exon (bracketed in FIG. 2) and the c-erbA/steroid receptor genes led us to compare the entire hap predicted amino acid sequence with hGR, rPR, hER, and hc-erbA/thyroid hormone receptor. The five sequences have been aligned for maximal homology by the introduction of gaps. The results are depicted in FIG. 6. Specifically, the following nucleotide sequences were aligned after a computer alignment of pairs (Wilbur and Lipman, 1983):

hap product, human placenta c-erbA protein (hc-erbA, Weinberger et al., 1986), human oestrogen receptor (hER, Green et al., 1986), rabbit progesterone receptor (rPR, Loosfelt et al., 1986), and human gluccocorticoid receptor (hGR, Hollenberg et al., 1985).

A minimal number of gaps (—) was introduced in the alignment.

Amino acid residues matched in at least three of the polypeptides are boxed in FIG. 6. The codes for amino acids are:

| | | |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |

| | | |
|---|---|---|
| P | Pro | Proline |
| Q | Gln | Glutamine |
| R | Arg | Arginine |
| S | Ser | Serine |
| T | Thr | Threonine |
| V | Val | Valine |
| W | Trp | Tyrptophan |
| Y | Tyr | Tyrosine. |

The sequence comparison analysis revealed that the two regions highly conserved in the thyroid/steroid hormone receptors are similarly conserved in the hap product. Consequently, the overall organization of hap is much similar to that of the four receptors in that it can be roughly divided into four regions (arbitrarily referred to as A/B, C, D and E (Krust et al., 1986)).

In C, the most highly conserved region, extending from amino-acid 81 to 146 in hap, the nine cysteines already conserved between the four known receptors are strikingly present at the same positions. Comparison between the cysteine-rich region of hap with the corresponding region of the four receptors reveals 64% amino acid identity with hc-erbA, 59% with hER, 42% with rPR and 44% with hGR. This is schematically represented in FIG. 7.

Figure 7:
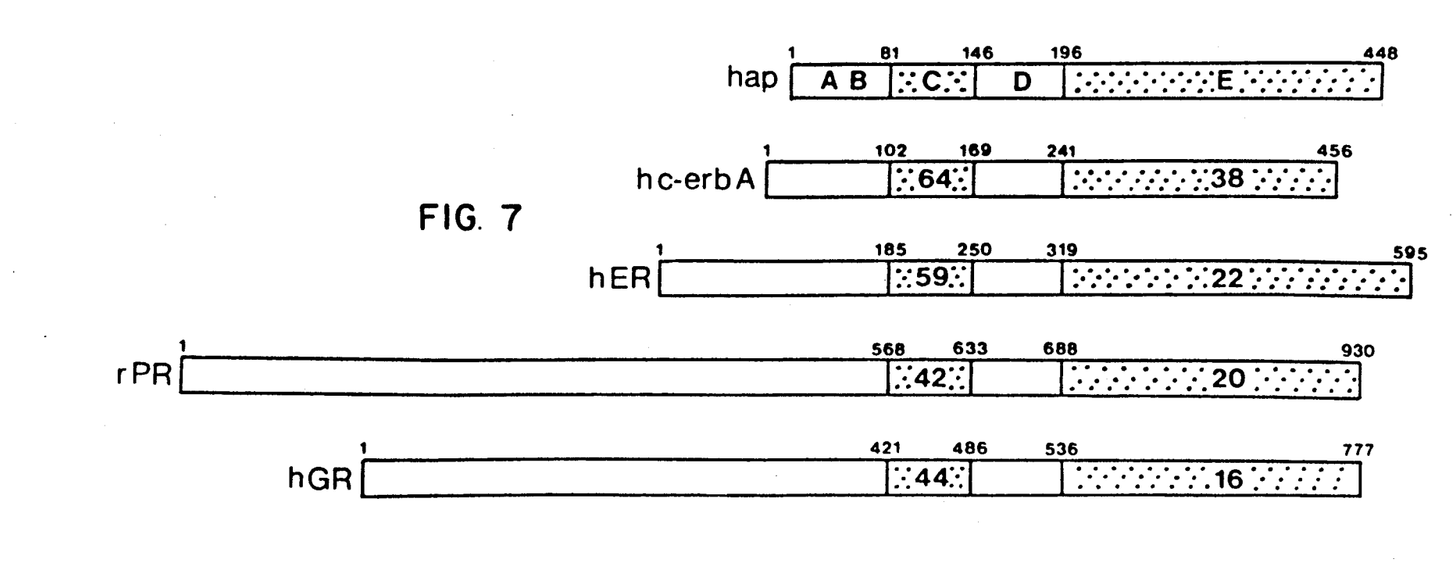
FIG. 7 is a schematic alignment of similar regions identified as A/B, C, D, and E of the amino acid sequences of FIG. 6.

Referring to FIG. 7, a schematic alignment of the five proteins can be seen. The division of the thyroid/steroid hormone receptor regions A/B, C, D, E is schematically represented in the hap protein. The two highly conserved regions, identified as the putative DNA-binding (region C) and hormone-binding (region E) domains of the receptors, are shown as stippled blocks. The numbers refer to the position of amino acid residues. The sequence of each of the hc-erbA product, hER, rPR and hGR receptors are compared with the hap protein. The numbers present in the stippled blocks correspond to the percentage of homology between hap protein on the one hand and each of the receptors on the other hand in the two highly conserved regions C and E. The empty blocks correspond to the non-conserved A/B and D regions.

It has also been found that hap shares 47% homology in the C region with the chicken vitamin D3 receptor (VDR), recently cloned as a partial cDNA (McDonnel et al., 1987) (data not shown). Apart from c-erbA, which contains two additional residues, the 66 amino acid long C region shows a constant length in hER, VDR, hGR, rPR and hap sequences.

Region E (residue 195–448), which is well-conserved, but to a lesser extent, shows a slightly stronger homology to hc-erbA (38%) (FIG. 7). The hap/hc-erbA homology, however, remains inferior to the identity found between hGR and rPR (90 and 51 per cent in regions C and E, respectively). No significant homology was observed when comparing the A/B (residue 1–80) and D (147–194) regions which are similarly variable, both in sequence and length, in the four known receptors.

It is thus evident from FIGS. 6 and 7 that the hap product exhibits two highly homologous regions. The C domain is characterized by strikingly conserved Cys-X2-Cys units, evoking those found in the DNA-binding transcriptional factor TFIIIA (Miller et al., 1985) and in some protein that regulated development, such as Kruppel (Rosenberg et al., 1986). In the latter, the Cys-X2-Cys, together with His-X3-His units, can form metal binding fingers that are crucial for DNA-binding (Berg, 1986; Diakun et al. 1986). Similarly, the C domain of previously cloned receptors are likely to contain metal binding fingers and were shown to the C region of the hap gene product shares 24/66 conserved amino acids with all all steroid or thyroid hormone receptors, including all nine cysteine residues, it is likely that the hap protein is a DNA-binding protein. Hap, as c-erbA/-steroid receptors, may modulate the transcription of target genes.

In addition, the significant homology detected in the E domain suggests that hap product is a ligand-binding protein and directs the question of the nature of the putative ligand. Hap protein seems to differ too much from previously cloned hormone receptors to be a variant of one of them. In addition, the in vitro translated 51 K hap polypeptide failed to bind all ligand tested. Although that hap gene product could be a ligand-independent DNA-binding protein, it is believed that hap encodes a receptor for a presently unidentified circulating or intracellular ligand.

It has been proposed that steroid and thyroid hormone receptor genes were derived from a common ancestor (Green and Chambon, 1986). This primordial gene may have provided to the receptors their common scaffolding while the hormone and target gene cellular DNA specificities were acquired through mutations accumulated in the C and E domains. Hap is both linked to the steroid receptor gene by its shorter C domain (66 AA) and to the thyroid hormone receptor genes by its clearly greater homology with c-erbA in the E region (38%). This suggests that hap ligand may belong to a different hormone family.

Different functions have been assigned to the four regions defined in the glucocorticoid and oestrogen receptors (Kumar et al., 1986; Giguere et al., 1986; Miesfeld et al., 1987). By analogy, the regions C and E may represent, respectively, the putative DNA-binding and hormone-binding domains of the hap protein. The precise functions of the A/B and D domains remain unknown. The presence of the amino-terminal A/B region of the human GR has been recently shown to be necessary for full transcriptional activity (Hollenberg et al., 1987), whereas results obtained with the rat GR indicated it was dispensable (Miesfeld et al., 1987). From this alignment study it appears that hap is distinct, but closely related to the thyroid/steroid hormone receptor genes suggesting that its product may be a novel ligand-dependent, DNA-binding protein.

Hap related genes

Southern blotting was performed on restriction enzyme-digested DNAs obtained from different organisms with labelled genomic MNT fragment containing the first exon of the cysteine-rich region of hap. The results are shown in FIG. 8. More particularly, hap related genes in vertebrates (A) and in humans (B and C) were compared. Cellular DNA (20 µg) from various source was digested with BqlII and subjected to Southern blot analysis using the MNT probe under non-stringent hybridization and washing conditions. The lanes in FIG. 8A are identified as follows:

Lane a human liver
Lane b domestic dog liver
Lane c woodchuck (*Marmota monax*)
Lane d mouse liver (BALB/c strain)
Lane e chicken erythrocytes
Lane f cartilaginous fish (Torpedo).

Figure 8A:
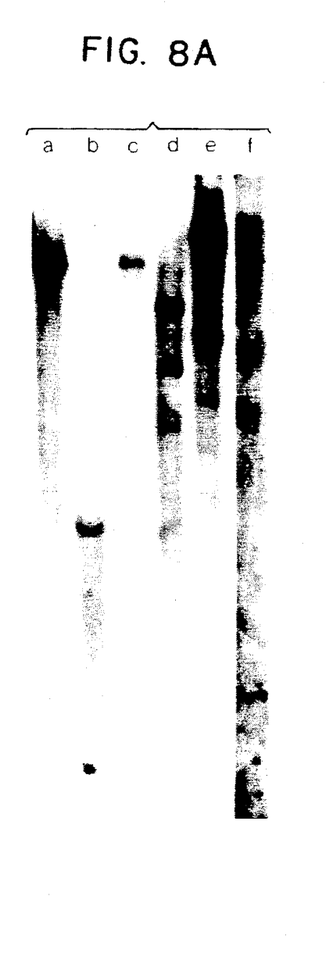
FIG. 8 depicts hap related genes in vertebrates (A) and in humans (B and C) as determined by Southern blot analysis.

As illustrated in FIG. 8A, BqlII fragments that anneal effectively with MNT probe under non-stringent hybridization and washing conditions are present in digests of DNA from several mammals (mouse, woodchuck, dog) as well as from bird and fish. If this blotting experiment is performed at high stringency, no hybridization is observed with heterologous DNA (data not shown) These data suggest that the hybridizing sequences represent evolutionarily conserved homologs of hap.

Figure 8B:
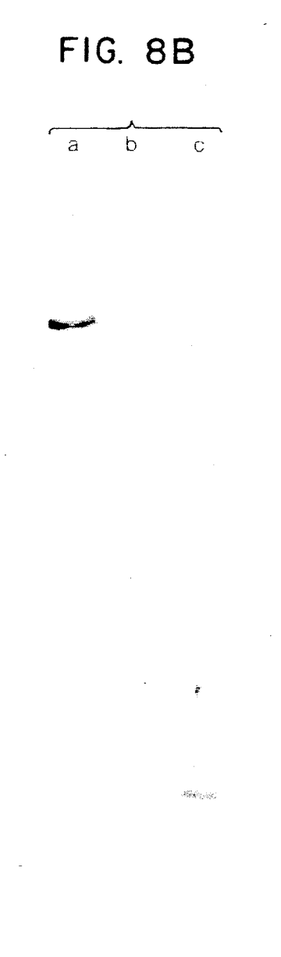

The existence of multiple c-erbA and GR genes (Jansson et al., 1983; Weinberger et al., 1986; Hollenberg et al., 1985) encouraged a search for hap related genes in the human genome. Thus, human liver DNA digested by PstI, BamHI, and EcoRI was analyzed by Southern blot, using the MNT probe, under stringent conditions. The results are shown in FIG. 8B. After digestion of liver DNA by PstI (lane a), BamHI (lane b), or EcoRI (lane c), a single band is observed with the MNT probe in high stringency hybridization.

Figure 8C:
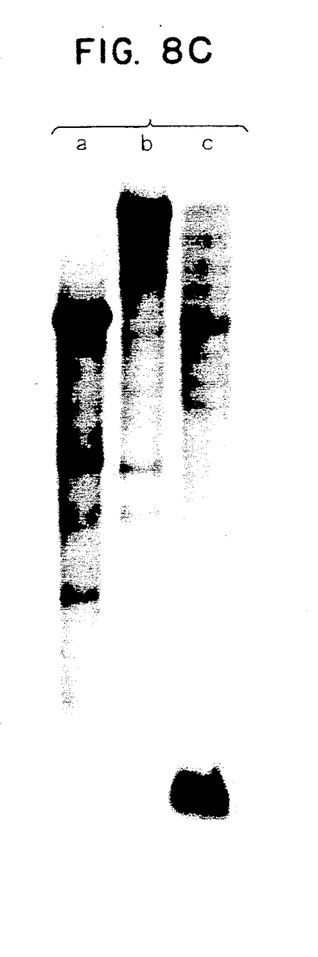

The same blot was hybridized with the MNT probe under nonstringent hybridization and washing conditions. The results are shown in FIG. 8C. When Southern blotting was performed under relaxed hybridization conditions, additional bands were observed in the products of each enzyme digestion (FIG. 8C, lanes a, b, c). For example, seven faint hybridizing fragments of 1, 1.7, 2.4, 3.8, 5.5, 6, 7.4 kb were observed in the BamHI digestion (lane b) None of those bands cross-hybridized with a human c-erbA probe (data not shown). A minimum of three faint bands in the PstI lane suggests the existence of at least four related hap genes in the human genome.

From a panel of somatic cell hybrids, hap was assigned to chromosome 3 (Dejean et al., 1986). To find out whether the hap related genes were all chromosomally linked or not, DNAs from human liver LA.56U and 53K cell-lines (two mouse/human somatic cell hybrids containing, altogether, most human chromosomes except chromosome 3 (Nguyen Van Cong et al., 1986)), and mouse lymphoid cells were BamHI digested, transferred to nitrocellulose, and hybridized to the MNT probe in low-stringency conditions. Of the seven faint bands present in the human liver DNA track, two at least were conserved in the LA.56U and/or L.53K cell line DNA digests (data not shown) indicating that some of the hap genes do not localize on chromosome 3. Altogether the results suggest that hap belongs to a multigene family consisting of at least four members dispersed in the human genome.

The experimental procedures used in carrying out this invention will now be described in greater detail.

EXPERIMENTAL PROCEDURES cDNA Cloning and Screening

Briefly, the cDNA was synthesized using oligo dT primed poly-A+ liver mRNA, using the method of Gubler and Hoffman (1983 (C. de Taisne, unpublished data). cDNAs were size selected on sucrose gradient and the fraction corresponding to a mean size o 3 kb was treated with EcoRI methylase. After addition of EcoRI linkers, the cDNA was digested by EcoRI and ligated to an EcoRI restricted lambda-NM1149. After in vitro encapsidation, the phages were amplified on C600 hfl and $2.10^6$ recombinant were plated at a density of 10,000 per dish. The dishes were transferred to nylon filters and hybridized to the 350 bp EcoRI-EcoRI genomic fragment (MNT) previously described (Dejean et al., 1986). Four positive clones were isolated and the restriction map of each insert was determined. The longest one, clone lambda-13, was subjected to nucleotide sequence analysis.

Nucleotide Sequence

Clone lambda-13 DNA was sonicated, treated with the Klenow fragment of DNA polymerase plus deoxyribonucleotides (2hr, 15° C.) and fractionated by agarose gel electrophoresis. Fragments of 400–700 bp were excised and electroeluted. DNA was ethanol-precipitated, ligated to dephosphorylated SmaI cleaved M13 mp8 replication form DNA and transfected into *Excherichia coli* strain TG-1 by the high-efficiency technique of Hanahan (1983). Recombinant clones were detected by plaque hybridization using either of the four EcoRI fragments of cDNA insert as probes (FIG. 1). Single-stranded templates were prepared from plaques exhibiting positive hybridization signals and were sequenced by the dideoxy chain termination procedure (Sanger et al., 1977) using buffer gradient gels (Biggin et al., 1983).

Northern Blots

Cytoplasmic RNA was isolated from the fresh tissue using guanidine thiocyanate, and the RNA cell line was extracted using isotonic buffer and 0.5% SDS, 10 mM Na acetate pH 5.2. RNAs were then treated with hot phenol. Poly(A)+ RNA (15 µg) of the different samples were separated on a 1% agarose gel containing glyoxal, transferred to nylon filters and probed using the nick-translated MNT fragment. The experimental procedure is described in Maniatis et al. (1982).

Southern Blot

20 µg of genomic DNA was digested to completion, fractionated on a 0.8% agarose gel and transferred to nylon paper. Low stringency hybridization was performed as follows: 24 hr prehybridization in 35% formamide, 5x Denhardt, 5x SSC, 300 µg/ml denatured salmon sperm DNA, at 40° C.; 48 hr hybridization with 35% formamide, 5x Denhardt, 5x SSC, 10% Dextran sulfate, $2.10^6$ cpm/ml denatured $^{32}$P labelled DNA probe (specific activity $5.10^8$cpm/µg) Washes were made in 2x SSC, 0.1 SDS, 55° C. for 15 min. High stringency hybridization conditions were the same except that 50% formamide was used with 24 hr hybridization. Washing was in 0.1x SSC, 0.1 SDS, 55° C. for 30 min.

Construction of Plasmids for In-Vitro Translation

The 3 kb insert of phage lambda-13 was excised from the phage DNA by partial EcoRI digestion, electroeluted and digested by BamHI and HindIII. To remove most of the untranslated sequences, the 1.8 kb cDNA fragment obtained was then partially digested by MaeI (Boehringer). The 1.4 kb MaeI-MaeI fragment, extending from the first to the third MaeI site in the cDNA insert sequence (FIG. 1) and containing the complete coding region was mixed with SmaI cut dephosphorylated pTZ18 (Pharmacia), the extremities were filled in using Klenow fragment of DNA PolI (Amersham) and ligated. Two plasmids were derived: pCOD20 (sense) and pCOD14 (antisense).

Translation and hormone binding assays pCOD20 and pCOD14 were linearized with HindIII. Capped mRN was generated using 5 µg of DNA, 5 µM rNTP, 25 mM DTT, 100 U RNAsin (Promega), 50 U T7 Pol (Genofit) in 40 mM Tris pH 8, 8 mM MgCl$_2$, 2 mM spermidine, 50 mM NaCl, in 100 μl at 37° C. Capping was performed by omitting GTP and adding CAP (m⁷ G (5′) ppp (5′) G) (Pharmacia) for the 15 first minutes of the reaction. Translation was performed using rabbit reticulocyte lysate (Amersham) under the suggested conditions using 40 μl of lystae for 2.5 μg of capped RNA.

The thyroid hormone binding assays included 5 μl of lysate in (0.25M sucrose, 0.25 KCl, 20 mM Tris (pH 7.5), 1 mM MgCl$_2$, 2 mM EDTA, 5 mM DTT) with 1 mM [$^{125}$I]T4, [$^{125}$I]T3 or [$^{125}$I]rT3 (specific activity: T4, rT3 1400 mCi/mg Amersham, T3 3000 mCi/mg NEN). After at least 2 hr of incubation at 0° C., free was separated from bound by filtration through millipore HAWP 02500 filters using 10 ml of ice cold buffer. For testosterone, retinol, retinoic acid 10 ul of lysate were added to 45 lambda of 20 mM Tris pH 7.3, 1 mM EDTA, 50 mM NaCl, 2 mM beta-mercaptoethanol an 5 mM testosterone, 400 mM retinol or 15 mM retinoic acid (81 Ci/mmol; 60 Ci/mmol; 46 Ci/mmol; Amersham). After an overnight incubation at 0° C. free was separated from bound by Dextran coated charcoal (0.5% Norit A - 0.05% T70) and centrifugation. All experiments were performed in duplicates and parallel experiment were performed with 100 fold excess corresponding cold hormone.

In summary, a hepatitis B virus (HBV) integration in a 147 bp cellular DNA fragment homologous to steroid receptors and c-erbA/thyroid hormone receptor genes previously isolated from a human hepatocellular carcinoma (HCC) was used as a probe to clone the corresponding complementary DNA from a human liver cDNA library. The nucleotide sequence analysis revealed that the overall structure of the cellular gene, named hap, is similar to that of DNA-binding hormone receptors. That is, it displays two highly conserved regions identified as the putative DNA-binding and hormone-binding domains of the c-erbA/steroid receptors. Six out of seven hepatoma and hepatoma-derived cell-lines express a 2.5 kb hap mRNA species which is undetectable in normal adult and fetal livers but present in all non-hepatic tissues analyzed. Low stringency hybridization experiments revealed the existence of hap related genes in the human genome. Taken together, the data suggest that the hap product may be a member of a new family of ligand-responsive regulatory proteins whose inappropriate expression in liver seems to correlate with the hepatocellular transformed state.

Because the known receptors control the expression of target genes that are crucial for cellular growth and differentiation, an altered receptor could participate in the cell transformation In that sense, avian v-erbA oncogene, which does not by itself induce neoplasms in animals, potentiates the erythroblast transformant effects of v-erbB and other oncogenes of the src family (Kahn et al., 1986). It has been shown that the v-erbA protein has lost its hormone-binding potential (Sap et al., 1986), presumably as a result of one or several mutations it has accumulated in its putative ligand-binding domain. It has been also suggested (Edwards et al., 1979) that the growth of human breast tumors are correlated to the presence of significant levels of ER. This invention may provide a novel example in which a DNA-binding protein would again relate to the oncogenic transformation by interfering with the transcriptional regulation of target genes. DNA-transfection assays using the native hap cDNA as well as 'altered' hap genes derived from various HCC can provide important information concerning any transforming capacity.

Following is a more detailed identification of the literature citations appearing above in parentheses:

Beasley, R. P., and Hwang, L. Y. (1984). Epidemiology of Hepatocellular Carcinoma In Viral Hepatitis and Liver Disease, G. N. Vyas, J. L. Dienstag, J. H. Hoofnagle, eds, (Grune and Stratton, Inc.), pp. 209-224.

Berg, J. M. (1986). More metal-binding fingers. Nature, 319, 264-265.

Biggin, M. D., Gibson, T. J. and Hong, G. F. (1983). Buffer gradient gels and $^{35}$S label as an aid to rapid DNA sequence determination. Proc. Natl. Acad. Sci. USA, 80, 3963-3965.

Brechot, C., Pourcel, C., Louise, A., Rain, B. and Tiollais, P. (1980). Presence of integrated hepatitis B virus DNA sequences in cellular DNA of human hepatocellular carcinoma. Nature, 286, 533-535.

Chakraborty, P. R., Ruiz-Opazo, N., Shouval, D. and Shafritz, D. A. (1980). Nature, 286, 531-533.

Chen, D. S., Hoyer, B. H., Nelson, J., Purcell, R. H. and Gerin, J. L. (1982). Detection and properties of hepatitis B viral DNA in liver tissues from patients with hepatocellular carcinoma. Hepatology, 2, 42S-45S.

Conneely, O. M., Sullivan, W. P., Toft, D. O., Birnbaumer, M., Cook R. G., Maxwell, B. L., Zarucid-Schulz, T., Greene, G. L., Schrader, W. T. and O'Malley, B. W. (1986). Molecular cloning of the chicken progesterone receptor. Science, 233, 767-770.

Dejean, A., Bougueleret, L., Grzeschik, K. H. and Tiollais, P. (1986). Hepatitis B virus DNA integration in a sequence homologous to v-erbA and steroid receptor genes in a hepatocellular carcinoma. Nature, 322, 70-72.

Diakun, G. P., Fairall, L. and Klug, A. (1986). EXAFS study of the zinc-binding sites in the protein transcription factor IIIA. Nature, 324, 698-699.

McDonnell, D. P., Mangelsdorf, D. J., pike, J. W., Haussler, M. R. and O'Malley, B. W. (1987). Molecular cloning of complementary DNA encoding the avian receptor for vitamin D. Science, 235, 1214-1217.

Edman, J. C., Gray, P., Valenzuela, P., Rall, L. B. and Rutter, W. J. (1980). Integration of hepatitis B virus sequences an their expression in a human hepatoma cell. Nature, 286, 535-538.

Edwards, D. P., Chamness, G. C., McGuire, W. L. (1979). Estrogen and progesterone receptor proteins in breast cancer. Biochimica et Biophysica Acta, 560, 457-486.

Giguere, V., Hollenberg, S. M., Rosenfeld, M. G. and Evans, R. M. (1986). Functional Domains of the human glucocorticoid receptor. Cell, 46, 645-652.

Green, S., Walter, P., Kumar, V., Krust, A., Bornert, J. M., Argos, P. and Chambon, P. (1986). Human oestrogen receptor cDNA: sequence, expression and homology to v-erb-A. Nature 320, 134-139.

Green, S. and Chambon, P. (1986). A superfamily of potentially oncogenic hormone receptors. Nature, 324, 615-617.

Greene, G L., Gilna, P., Waterfield, M., Baker, A., Hort, Y. and Shine, J. (1986). Sequence and expression of human estrogen receptor complementary DNA, Science, 231, 1150-1154.

Gubler, U. and Hoffman, B. J. (1983). A simple and very efficient method for generating cDNA libraries. Gene, 25, 263–269.

Hanahan, D. (1983). Studies on transformation of *Escherichia coli* with plasmids. J. Mol. Biol. 166, 557–580.

Hollenberg, S. M., Weinberger, C., Ong., E. S., Cerelli, G., Oro, A., Lebo, R., Thompson, E. G., Rosenfeld, M. G. and Evans, R. M. (1985). Primary structure and expression of a functional human glucocorticoid receptor. Cell, 49, 39–46.

Jansson, M., Philipson, L. and Vennstrom, B. (1983). Isolation and characterization of multiple human genes homologous to the oncogenes of avian erythroblastosis virus. The EMBO J. 2, 561–565.

Kahn, P., Frykberg, L., Brady, C., Stanley, I., Beug, H., Vennstrom, B. and Graf, T. (1986). v-erbA cooperates with sarcoma oncogenes in leukemic cell transformation. Cell, 45, 349–356.

Kozak, M., (1986). Bifunctional messenger RNAs in eukaryotes. Cell, 47, 481–483.

Krust, A., Green,, S., Argos, P., Kumar, V., Walter, P., Bornert J. M. and Chambon, P. (1986). The chicken oestrogen receptor sequence: homology with v-erbA and the human oestrogen and glucocorticoid receptors. The EMBO J., 5, 891–897.

Kumar, V., Green, S., Staub, A. and Chambon, P. (1986). Localisation of the oestradiol-binding and putative DNA-binding domains of the human oestrogen receptor. The EMBO J., 5, 2231–2236.

Loosfelt, H., Atger, M., Misrahi, M., Guiochon-Mantel, A., Meriel, C., Logeat, F., Bernarous, R. and Milgrom, E. (1986). Cloning and sequence analysis of rabbit progesterone-receptor complementary DNA. Proc. Natl. Acad. Sci. USA, 83, 9045–9049.

Maniatis, T., Fritch, E. and Sambrook, J. (1982). Molecular cloning: a laboratory manual (Cold Spring Harbor, New-York Cold Spring Harbor Laboratory).

Miesfeld, R., Rusconi, S., Godowski, P. J., Maler, B. A., Okret, S., Wilkstrom, A. C., Gustafsson, J. A. and Yamamoto, K. R. (1986). Genetic complementation of a glucocorticoid receptor deficiency by expression of cloned receptor cDNA. Cell, 46, 389–399.

Miesfeld, R., Godowski, P. J., Maler, B. A. and Yamamoto, K. R. (1987. Glucocorticoid receptor mutants that define a small region sufficient for enhancer activation. Science, 236, 423–427.

Miller, J., McLachlan, A. D. and Klug, A. (1985). Repetitive zinc-binding domains in the protein transcription factor IIIA from Xenopus oocytes. The EMBO J., 4, 1609–1614.

Nguyen Van Cong, Weil, D., Finaz, C., Cohen-Haguenauer, O., Gross, M. S., Jegou-Foubert, C., de Tand, M. F., Cochet, C., de Grouchy, J., Frezal, J. (1986). Panel of twenty-five independent man-rodent hybrids for human genetic marker mapping. Ann. Genet., 29, 20–26.

Rosenberg, U. G., Schroder, C., Preiss, A., Kienlin,, A., Cote, S., Riede, I. and Jackle, H. (1986). Structural homology of the product of the Drosophila Kruppel gene with Xenopus transcription factor IIIA. Nature, 319, 336–339.

Sanger, F., Nicklen,, S. and Coulson,, A. R. (1977). DNA sequencing with chain-terminating inhibitors. Proc. Natl. Acad. Sci. USA, 74, 5463–5467.

Sap, J., Munoz, A., Damm, K., Goldberg, Y., Ghysdael, J., Leutz, A., Beug, H. and Vennstrom, B. (1986). The c-erb-A protein is a high affinity receptor for thyroid hormone. Nature, 324, 635–640.

Szmuness, W. (1973). Hepatocellular carcinoma and the hepatitis B virus evidence for a causal association. Prog. Med. Virol., 24, 40–69.

Tiollais, P., Pourcel, C. and Dejean, A. (1985). The hepatitis B virus. Nature, 317, 489–495.

Weinberger, C., Thompson, C. C., Ong, E. S., Lebo, R., Gruol, D. J. and Evans, R. M. (1986). The c-erb-A gene encodes a thyroid hormone receptor. Nature, 324, 641–646.

Wilbur, W. J. and Lipman, D. J. (1983). Rapid similarity searches of nucleic acid and protein data banks. Proc. Natl. Acad. Sci. USA, 80, 726–730.

Yamamoto, K. R. (1985). Steroid receptor regulated transcription of specific genes and gene networks. Ann. Rev. Genet., 19, 209–252.

What is claimed is:

1. A polypeptide of hap protein, wherein the polypeptide consists essentially of an amino acid sequence selected from the group consisting of:

a) GlnHisArgHisThrAlaGlnSerIleGluThrGlnSerThrSerSerGlu
GluLeuValProSerProProSerProLeuProProProArgValTyrLysPro
CysPheValGlnAspLysSerSerGlyTyrHisTyrGlyValSerAlaCysGlu
GlyCysLysGlyPheArgArgSerIleGlnLysAsnMetIleTyrThrCysHis
ArgAspLysAsnCysValIleLysValThrArgAsnArgCysGlnTyrCys
ArgLeuGlnLysCysPheGluValGlyMetLysGluSerValArgAsnAsp
ArgAsnLysLysLysLysGluThrSerLysGlnGluCysGluSerTyrGlu
MetThrAlaGluLeuAspAspLeuThrGluLysIleArgLysAlaHisGluThr
PheProSerLeuCys;
b) ValArgAsnAspArgAsnLysLysLysLysGluThrSerLysGlnGlnCys
c) AsnAspArgAsnLysLysLysLysGluThrCys
d) CysGlyValSerGlnSerProLeuValGln and
e) AlaGluLeuAspAspLeuThrGluLysIleArg;

linked to a carrier molecule.

2. A polypeptide as claimed in claim 1, wherein the polypeptide consists essentially of the amino acid sequence:

GlnHisArgHisThrAlaGlnSerIleGluThrGlnSerThrSerSerGluGlu
LeuValProSerProProSerProLeuProProProArgValTyrLysProCysPheVal
GlnAspLysSerSerGlyTyrHisTyrGlyValSerAlaCysGluGlyCysLysGlyPhe
ArgArgSerIleGlnLysAsnMetIleTyrThrCysHisArgAspLysAsnCysValIle
LysValThrArgAsnArgCysGlnTyrCysArgLeuGlnLysCysPheGluValGlyMet
LysGluSerValArgAsnAspArgAsnLysLysLysLysGluThrSerLysGlnGluCys
GluSerTyrGluMetThrAlaGluLeuAspAspLeuThrGluLysIleArgLysAlaHis
GluThrPheProSerLeuCys

3. A polypeptide as claimed in claim 1, wherein the polypeptide consists essentially of the amino acid sequence:

ValArgAsnAspArgAsnLysLysLysLysGluThrSer-
LysGlnGluCys linked to a carrier molecule.

4. A polypeptide as claimed in claim 1, wherein the polypeptide consists essentially of the amino acid sequence:

AsnAspArgAsnLysLysLysLysGluThrCys linked to a carrier molecule.

5. A polypeptide as claimed in claim 1, wherein the polypeptide consists essentially of the amino acid sequence:

CysGlyValSerGlnSerProLeuValGln linked to a carrier molecule.

6. A polypeptide as claimed in claim 1, wherein the polypeptide consists essentially of the amino acid sequence:

AlaGluLeuAspAspLeuThrGluLysIleArg linked to a carrier molecule.

7. A polypeptide of hap protein, wherein the polypeptide consists essentially of an amino acid sequence selected from the group consisting of:

a) GlnHisArgHisThrAlaGlnSerIleGluThrGlnSerThrSerSerGluGlu
LeuValProSerProProSerProLeuProProProArgValTyrLysProCysPheVal
GlnAspLysSerSerGlyTyrHisTyrGlyValSerAlaCysGluGlyCysLysGlyPhe
ArgArgSerIleGlnLysAsnMetIleTyrThrCysHisArgAspLysAsnCysValIle
LysValThrArgAsnArgCysGlnTyrCysArgLeuGlnLysCysPheGluValGlyMet
LysGluSerValArgAsnAspArgAsnLysLysLysLysGluThrSerLysGLnGluCys
GluSerTyrGluMetThrAlaGluLeuAspAspLeuThrGluLysIleArgLysAlaHis
GluThrPheProSerLeuCys;
b) ValArgAsnAspArgAsnLysLysLysLysGluThrSerLysGlnGluCys;
c) AsnAspArgAsnLysLysLysGluThrCys;
d) CysGlyValSerGlnSerProLeuValGln; and
e) AlaGluLeuAspAspLeuThrGluLysIleArg.

8. A polypeptide as claimed in claim 7, wherein said polypeptide consists essentially of the amino acid sequence:

GlnHisArgHisThrAlaGlnSerIleGluThrGlnSerThrSerSerGluGlu
LeuValProSerProProSerProLeuProProProArgValTyrLysProCysPheVal
GlnAspLysSerSerGlyTyrHisTyrGlyValSerAlaCysGluGlyCysLysGlyPhe
ArgArgSerIleGlnLysAsnMetIleTyrThrCysHisArgAspLysAsnCysValIle
LysValThrArgAsnArgCysGlnTyrCysArgLeuGlnLysCysPheGluValGlyMet
LysGluSerValArgAsnAspArgAsnLysLysLysLysGluThrSerLysGlnGluCys
GluSerTyrGluMetThrAlaGluLeuAspAspLeuThrGluLysIleArgLysAlaHis
GluThrPheProSerLeuCys.

9. A polypeptide as claimed in claim 7, wherein said polypeptide consists essentially of the amino acid sequence:

ValArgAsnAspArgAsnLysLysLysLysGluThrSerLysGlnGluCys.

10. A polypeptide as claimed in claim 7, wherein said polypeptide consists essentially of the amino acid sequence:

AsnAspArgAsnLysLysLysLysGluThrCys.

11. A polypeptide as claimed in claim 7, wherein said polypeptide consists essentially of the amino acid sequence:

CysGlyValSerGlnSerProLeuValGln.

12. A polypeptide as claimed in claim 7, wherein said polypeptide consists essentially of the amino acid sequence:

AlaGluLeuAspAspLeuThrGluCysIleArg.

* * * * *

UNITED STATES PATENT AND TRADEMARK OFFICE
CERTIFICATE OF CORRECTION

PATENT NO. : 5,149,781

DATED : September 22, 1992

INVENTOR(S) : Blaudin de The et al.

It is certified that error appears in the above-identified patent and that said Letters Patent is hereby corrected as shown below:

Column 20, line 58
Claim 2, after the sequence listing insert:

--linked to a carrier molecule.--

Signed and Sealed this

Twelfth Day of October, 1993

*Attest:*

BRUCE LEHMAN

*Attesting Officer*     *Commissioner of Patents and Trademarks*